US010495868B2

(12) United States Patent
Lin et al.

(10) Patent No.: US 10,495,868 B2
(45) Date of Patent: Dec. 3, 2019

(54) SAMPLE CARRYING MODULE AND PORTABLE MICROSCOPE USING THE SAME

(71) Applicant: Aidmics Biotechnology Co., Ltd., Taipei (TW)

(72) Inventors: Cheng-Ming Lin, Taipei (TW); Chang-Yu Chen, Taipei (TW); Tsun-Chao Chiang, Taipei (TW); Shu-Sheng Lin, Taipei (TW)

(73) Assignee: AIDMICS BIOTECHNOLOGY CO., LTD., Taipei (TW)

( * ) Notice: Subject to any disclaimer, the term of this patent is extended or adjusted under 35 U.S.C. 154(b) by 120 days.

(21) Appl. No.: 15/416,386

(22) Filed: Jan. 26, 2017

(65) Prior Publication Data

US 2017/0227756 A1    Aug. 10, 2017

(30) Foreign Application Priority Data

Feb. 5, 2016   (CN) .......................... 2016 1 0083284
Jan. 10, 2017  (CN) .......................... 2017 1 0015923

(51) Int. Cl.
*G02B 25/00*   (2006.01)
*G02B 25/02*   (2006.01)
(Continued)

(52) U.S. Cl.
CPC .......... *G02B 25/002* (2013.01); *G01N 21/03* (2013.01); *G02B 25/02* (2013.01); *G02B 27/286* (2013.01); *G01N 2021/0367* (2013.01)

(58) Field of Classification Search
CPC ............... G02B 21/00; G02B 21/0004; G02B 21/0008; G02B 21/241; G02B 21/34; G02B 21/36; G02B 21/361
(Continued)

(56) References Cited

U.S. PATENT DOCUMENTS 3,551,023 A    12/1970  Brackett
4,190,314 A *   2/1980  Goldsmith ............. G02B 21/34
                                             359/397
(Continued)

FOREIGN PATENT DOCUMENTS

CN    201508433 U     6/2010
DE    102013224172 A1  5/2015
(Continued)

*Primary Examiner* — Robert E. Tallman
(74) *Attorney, Agent, or Firm* — Muncy, Geissler, Olds & Lowe, P.C.

(57) ABSTRACT

A microscope apparatus includes a sample carrying module, a light source module and a lens module. The sample carrying module includes an adhesive element and a body having a light-transmission region and a sample viewing surface. The adhesive element is detachably adhered to the body, and at least partially covers the light-transmission region, such that the adhesive element is disposed adjacent to the sample viewing surface. The light source module is detachably disposed at a side of the body, and includes a base and a light source. The base has an aperture, and the sample carrying module is detachably disposed at a side of the aperture. The light source is disposed in the base. The lens module includes at least one lens, which is detachably disposed at one side of the sample carrying module and substantially focuses at the sample viewing surface, and corresponds to the light source module.

19 Claims, 13 Drawing Sheets

(51) Int. Cl.
*G02B 27/28* (2006.01)
*G01N 21/03* (2006.01)

(58) Field of Classification Search
USPC .............. 359/368, 391, 392, 396, 398, 801
See application file for complete search history.

(56) References Cited

U.S. PATENT DOCUMENTS

| | | | |
|---|---|---|---|
| 5,571,721 A | 11/1996 | Turner | |
| 5,812,312 A * | 9/1998 | Lorincz | G01N 1/30 |
| | | | 359/396 |
| 6,052,224 A | 4/2000 | Richardson | |
| 2001/0050810 A1 | 12/2001 | Lorincz | |
| 2003/0021021 A1 * | 1/2003 | Branch | G02B 21/34 |
| | | | 359/396 |
| 2004/0189988 A1 | 9/2004 | Scaduto | |
| 2010/0073766 A1 * | 3/2010 | Angros | B01L 3/545 |
| | | | 359/397 |
| 2010/0091364 A1 * | 4/2010 | Wozniak | G02B 21/34 |
| | | | 359/397 |
| 2012/0157160 A1 | 6/2012 | Ozcan et al. | |
| 2014/0120982 A1 * | 5/2014 | Fletcher | G02B 21/0008 |
| | | | 455/556.1 |
| 2016/0004057 A1 | 1/2016 | Lin et al. | |
| 2017/0160534 A1 * | 6/2017 | Fan | G02B 21/362 |

FOREIGN PATENT DOCUMENTS

| | | |
|---|---|---|
| JP | S 57-051911 U | 3/1982 |
| JP | H 11133308 A | 5/1999 |
| JP | 2001515211 A | 9/2001 |
| JP | 2004085272 A | 3/2004 |
| JP | 2016018215 A | 2/2016 |
| TW | M444520 | 1/2013 |

\* cited by examiner

SAMPLE CARRYING MODULE AND PORTABLE MICROSCOPE USING THE SAME

CROSS REFERENCE TO RELATED APPLICATIONS

This Non-provisional application claims priority under 35 U.S.C. § 119(a) on Patent Application No(s). 201610083284.4 filed in People's Republic of China on Feb. 5, 2016, and 201710015923.8 filed in People's Republic of China on Jan. 10, 2017, the entire contents of which are hereby incorporated by reference.

BACKGROUND OF THE INVENTION

Field of Invention

The present invention relates to a portable microscope apparatus capable of being cooperated with a smart communication device.

Related Art

The conventional microscope is usually applied for observing micro-organisms, cells or the fine structures of some materials. For the sake of easy observation, it is necessary to prepare the sample slices, which are light permeable. Afterwards, the sample slice is placed on a glass slide, and a small amount of liquid (the liquid is usually water) is dropped on the glass slide. Then, a cover glass is placed on the glass slide to cover the sample slice. Accordingly, the sample for observation with microscope is prepared. If the sample must be preserved, it is needed to encapsulate the prepared sample with proper material, thereby making the desired specimen.

For the science and research purposes, it is desired to observe the fine structures and textures for various kinds of bio or non-bio samples around the users, such as hair, fabric, blood, or the likes. Accordingly, the portable microscope apparatus is disclosed. For example, US Patent Application No. US2012/0157160 discloses a compact wide-field fluorescent imaging on a mobile device, TWM444,520 discloses a compact high magnification microscope lens, and CN200920005757.4 discloses a multifunction microscope apparatus. Unfortunately, although the portable microscope apparatus is available, the preparation of the samples is still very complex. This complex sample preparation method can limit the purpose of observation everywhere by microscope. Accordingly, it is desired to provide a sample carrying module, which can cooperate with the portable microscope apparatus for the purpose of observation everywhere.

SUMMARY OF THE INVENTION

An objective of the present invention is to provide a sample carrying module that can cooperate with the portable microscope apparatus.

To achieve the above objective, the present invention discloses a portable microscope apparatus, which is cooperated with an image capture module and includes a sample carrying module, a light source module and a lens module. The sample carrying module includes a body and an adhesive element. The body has a light-transmission region and a sample viewing surface, and the adhesive element is detachably adhered to the body and at least partially covers the light-transmission region. The adhesive element is disposed adjacent to the sample viewing surface. The light source module is detachably disposed at one side of the body, and includes a base and a light source. The base has an aperture, the sample carrying module is detachably disposed at one side of the aperture, and the light source is disposed in the base. The lens module includes at least one lens. The lens module substantially focuses at the sample viewing surface, corresponds to the light source module, and is detachably disposed at one side of the sample carrying module. The adhesive element is placed on a sample to stick the sample, and then attached to the body. Then, the light source module is assembled at one side of the sample carrying module and turned on. Afterwards, the lens module is assembled at the other side of the sample carrying module. Accordingly, the light emitted from the light source module can penetrate through the sample and reach the lens module. Thus, the operator can operate the image capture module to take the image of sample through the lens module.

In one embodiment, the adhesive element is a transparent element.

In one embodiment, the adhesive element is a sticker.

In one embodiment, the adhesive element is a transparent element and has a sample attaching surface configured with an adhesive region and a non-adhesive region.

In one embodiment, the adhesive element an adhesive region and a non-adhesive region, and the adhesive region includes a transparent area and a nontransparent area.

In one embodiment, the adhesive element is a transparent element and has a sample attaching surface configured with an adhesive region and a non-adhesive region, and the adhesive region has a pattern for assisting observation.

In one embodiment, the sample carrying module further includes at least one first magnetic element disposed at one side of the body.

In one embodiment, the sample carrying module further includes at least one first magnetic element disposed at one side of the body and magnetically connected to the light source module or the lens module.

In one embodiment, the light source module further includes a second magnetic element disposed in the base and magnetically connected to the sample carrying module or the lens module.

In one embodiment, the lens module further includes a third magnetic element magnetically connected to the sample carrying module or the light source module.

In one embodiment, the sample carrying module further includes at least one glass slide disposed at one side of the body.

In one embodiment, the sample carrying module further includes at least one glass slide disposed at one side of the body, and the adhesive element is detachably adhered to the glass slide.

In one embodiment, the body has a protrusion portion disposed at one side of the body.

In one embodiment, the base has a restriction portion, and the sample carrying module is detachably disposed in the restriction portion.

In one embodiment, the portable microscope apparatus further includes a fixing assembly for relatively fixing the lens module and the image capturing module.

In one embodiment, the image capturing module is configured in a smart phone, a tablet computer, a notebook computer, a traffic recorder, a camera or a selfie maker.

In one embodiment, the portable microscope apparatus further includes a first polarizer and a second polarizer disposed on optical paths at two sides of the sample carrying module, respectively.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
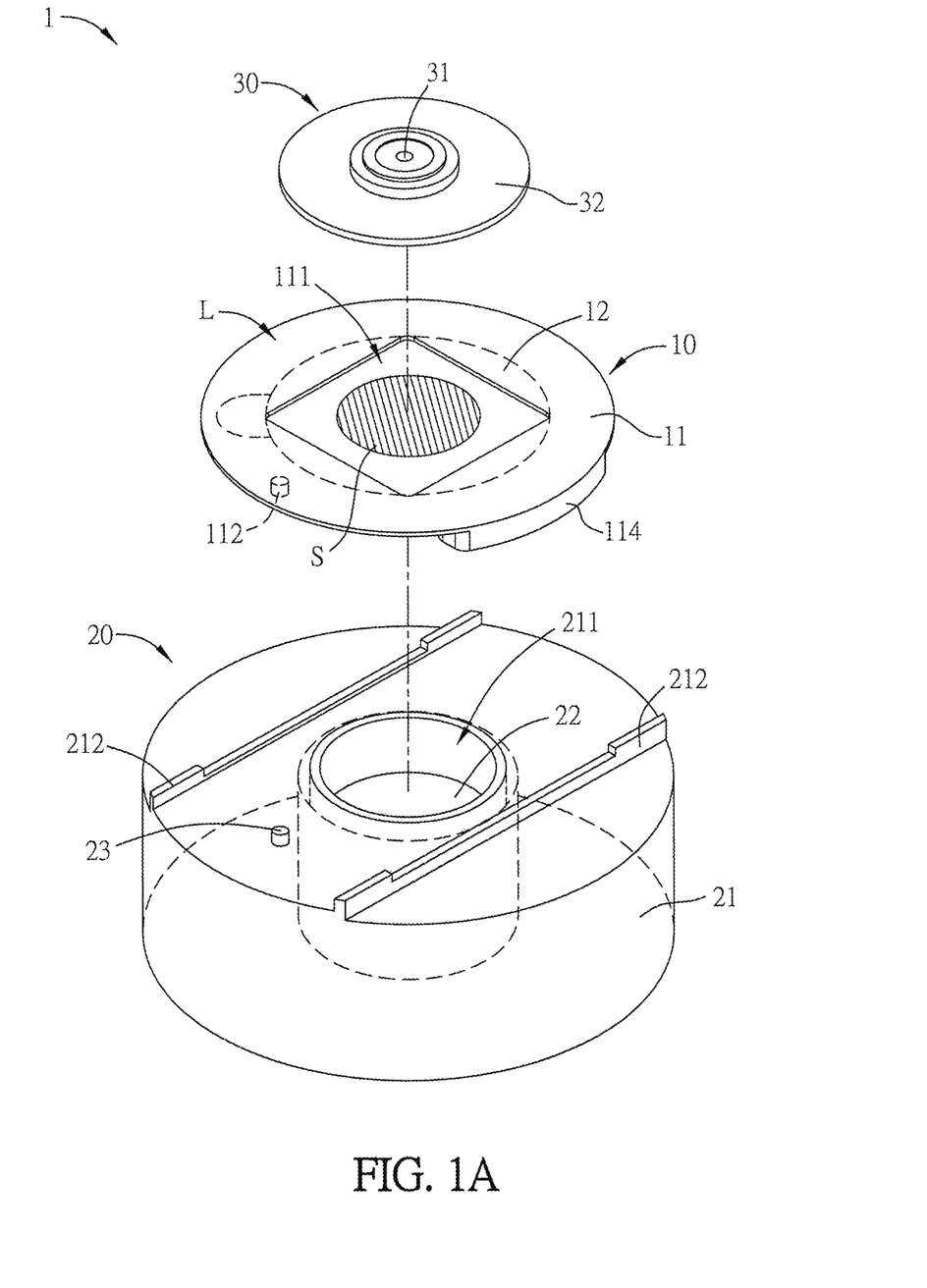
FIG. 1A is an exploded view of a portable microscope apparatus according to an embodiment of the invention.
Figure 1B:
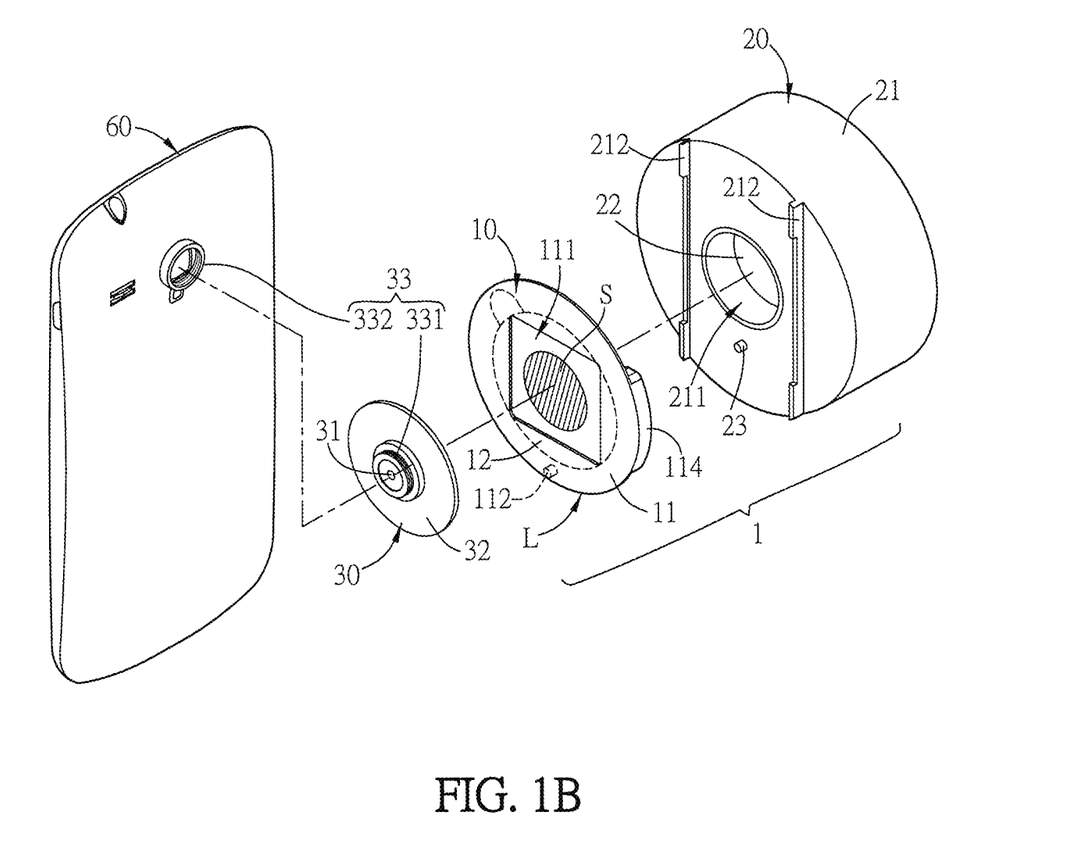
FIG. 1B is an exploded view of the portable microscope apparatus in cooperated with a portable electronic device according to an embodiment of the invention.

FIG. 1A is an exploded view of a portable microscope apparatus according to an embodiment of the invention, and FIG. 1B is an exploded view of the portable microscope apparatus in cooperated with a portable electronic device according to an embodiment of the invention. Referring to FIGS. 1A and 1B, a portable microscope apparatus 1 is cooperated with an image capture module 61 of a portable electronic device 60. For example, the portable electronic device 60 can be a smart phone, a tablet computer, a notebook computer, a traffic recorder, a camera or a selfie maker. The portable microscope apparatus 1 includes a sample carrying module 10, a light source module 20, and a lens module 30.

The sample carrying module 10 includes a body 11 and an adhesive element 12. The body 11 can be a carrier for carrying the adhesive element 12 and a to-be-detected sample S. In this embodiment, the body 11 is a metal plate. The body 11 has a light-transmission region 111, a protrusion portion 112, a limiting member 114, and a sample viewing surface L. The adhesive element 12 is a transparent element with a transmittance of greater than 90%. The adhesive element 12 can be a sticker, tape, or resin. The adhesive element 12 has a sample attaching surface for sticking the sample S, thereby forming an observable specimen. The adhesive element 12 is detachably adhered to the body 11 and at least partially covers the light-transmission region 111. As shown in figures, the adhesive element 12 is disposed adjacent to the sample viewing surface L. In this embodiment, the light-transmission region 111 can be passed by light. For example, the light-transmission region 111 may have an opening or a light-permeable material. In this embodiment, the light-transmission region 111 is configured with a hole.

The light source module 20 is detachably disposed at one side of the body 11 of the sample carrying module 10, and includes a base 21, a light source 22, and a switch 23. The base 21 has a hollow structure for accommodating the light source 22 and other related circuits. The base 21 has an aperture 211 and a restriction portion 212, which are disposed at the same side of the base 21. The light source 22 is coupled to the switch 23 and can emit light through the aperture 211 to the base 21. The restriction portion 212 has a slot C (see FIG. 4). When the sample carrying module 10 is detachably disposed on the restriction portion 212, it can be engaged with the slot C. In this case, the protrusion portion 112 can correspondingly press the switch 23 so as to turn on the light source 22 to emit light. In this embodiment, the light source 22 can emit visible light. However, in other embodiments, the light source 22 can emit invisible light such as infrared light, UV light or Raman light, which can be sensed by the sensing element of the image capture module 61. For example, when the light source 22 is a UV light source, the portable microscope apparatus 1 can be a fluorescent detector for counting the amount of bio cells.

The lens module 30 includes a lens 31 and a lens base 32. The lens 31 is embedded in the lens base 32. The lens module 30 is detachably disposed at one side of the sample carrying module 10 and substantially focuses at the sample viewing surface L. The lens module 30 corresponds to the light source module 20 (see FIG. 1A). That is, the light source module 20 and the lens module 30 are disposed at opposite sides of the sample carrying module 10. Referring to FIG. 1B, the portable microscope apparatus 1 further includes a fixing assembly 33, which includes a male fixing member 331 disposed on the lens base 32 and a female fixing member 332 disposed on the image capturing module 61, correspondingly. In this embodiment, the male fixing member 331 and the female fixing member 332 have corresponding threads for connecting to each other, thereby fixing the relative positions of the lens module 30a and the image capture module 61. To be noted, this embodiment is for an illustration only and is not to limit the scope of the invention. For example, the fixing assembly 33 can be an adhesive agent, clipper, magnet, sucker, latch, or the likes. In addition, as shown in FIG. 1B, the fixing assembly 33 can be integrated in the back cover or protection cover of the smart phone.

Figure 1C:
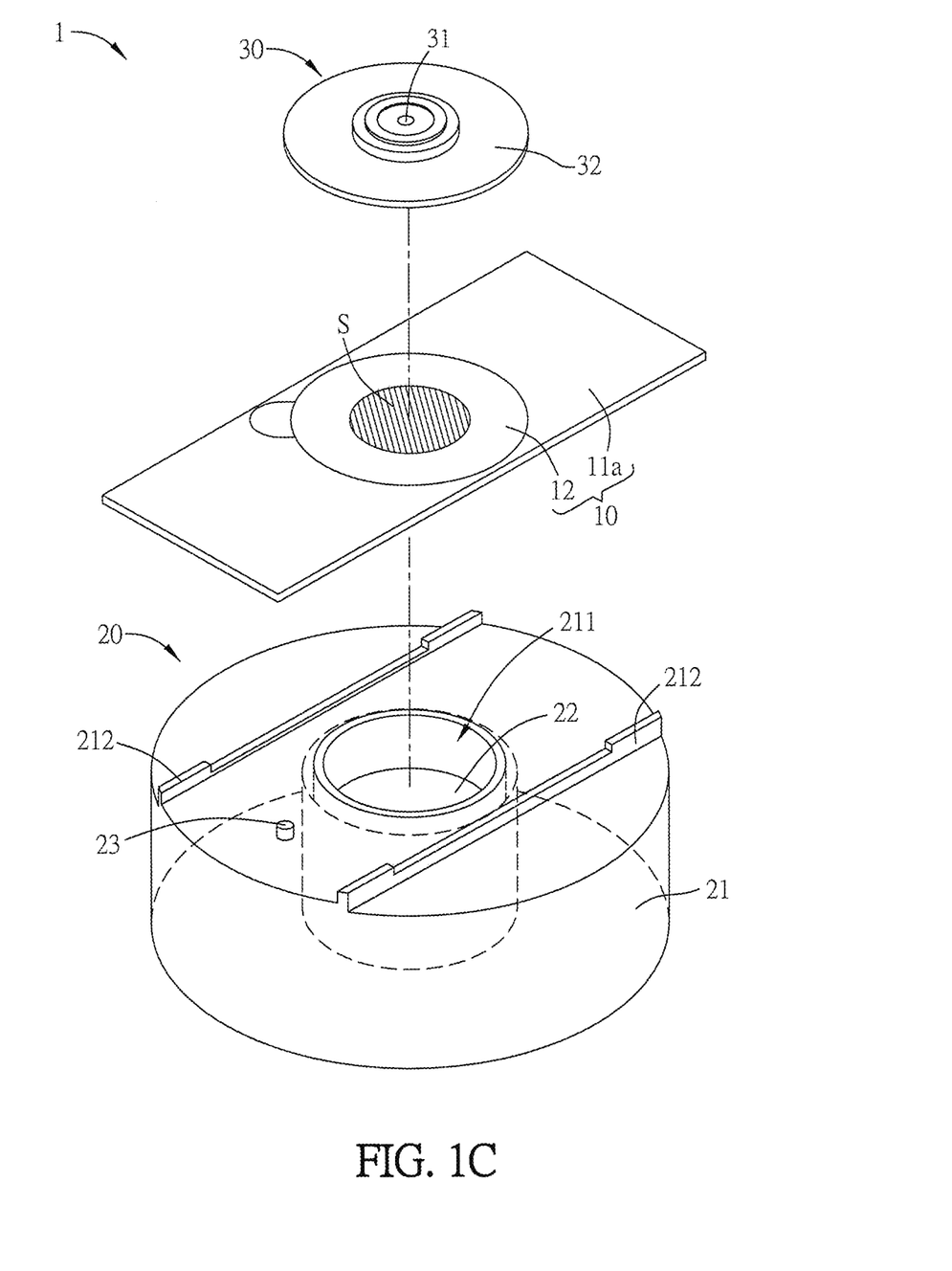
FIG. 1C is an exploded view of a portable microscope apparatus according to another embodiment of the invention.

FIG. 1C is an exploded view of a portable microscope apparatus according to another embodiment of the invention. As shown in FIG. 1C, the body 11a is a glass slide. In this embodiment, the operator can directly attach the adhesive element 12, which is adhered with the sample S, to the glass slide, and then engage the glass slide to the restriction portion 212 of the base 21, thereby finishing the configuration of the sample S.

Figure 1D:
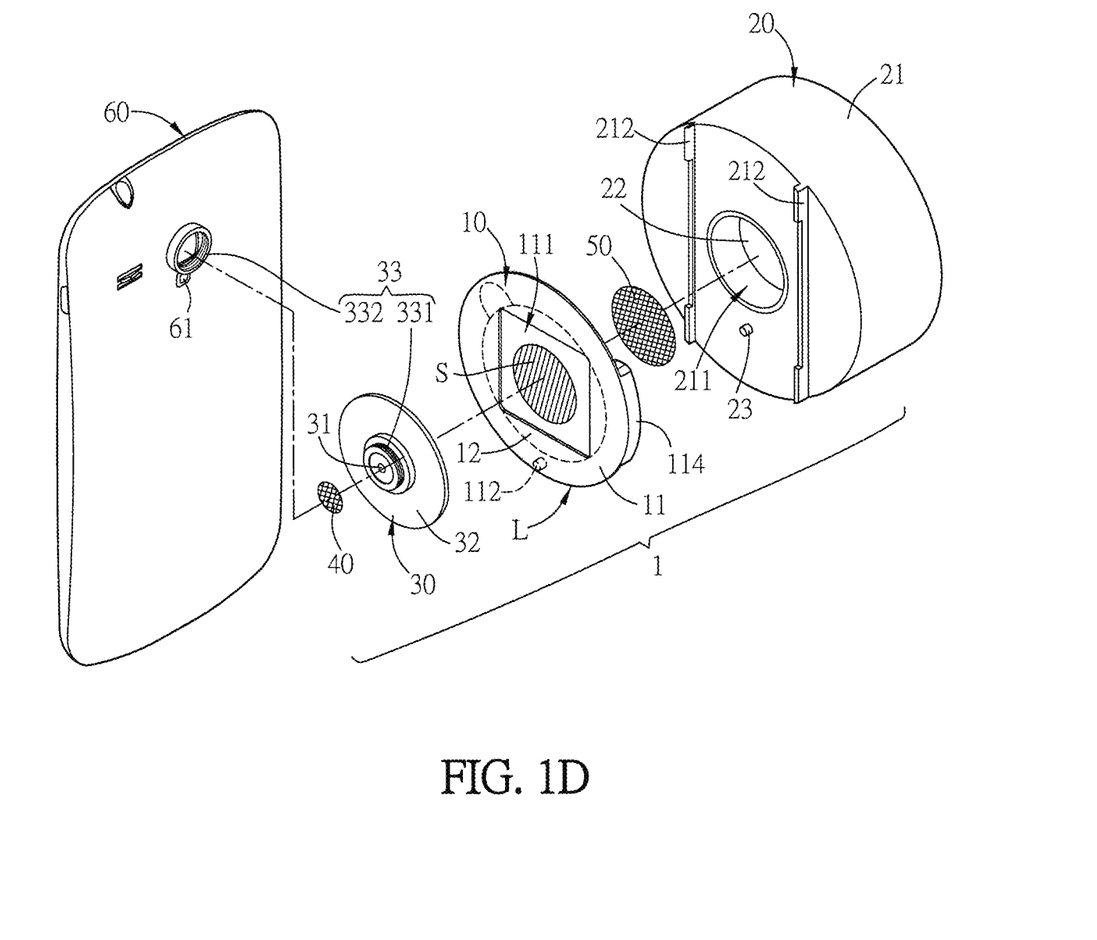
FIG. 1D is an exploded view of the portable microscope apparatus in cooperated with a portable electronic device according to another embodiment of the invention.

FIG. 1D is an exploded view of the portable microscope apparatus in cooperated with a portable electronic device according to another embodiment of the invention. As shown in FIG. 1D, the portable microscope apparatus 1 further includes a first polarizer 40 and a second polarizer 50, which are disposed on optical paths at two sides of the sample carrying module 10, respectively, for observing the sample S with birefringence property. For example, the sample S with birefringence property can be starch crystals or compound eyes of insects. The first polarizer 40 and the second polarizer 50 can be linear polarizers. In general cases, the directions of polarization axes of the first polarizer 40 and the second polarizer 50 are perpendicular to each other. In addition, the first polarizer 40 and the second polarizer 50 can be circular polarizers or elliptical polarizers.

The first polarizer 40 is disposed on an optical path between the sample S and the image capture module 61, and the second polarizer 50 is disposed on an optical path between the sample S and the light source module 20. In this embodiment, the first polarizer 40 is disposed between the lens module 30 and the image capture module 61. In practice, the first polarizer 40 is installed on the lens module 30, and then they are together fixed on the image capture module 61. That is, the first polarizer 40 is directly attached to the image capture module 61. The second polarizer 50 is disposed between the sample carrying module 10 and the light source module 20. For example, the second polarizer 50 is installed on the aperture 211 or attached to one side of the sample carrying module 10 closer to the aperture 211.

When the light source module 20 is turned on, the operator may not observe the image of the sample S if the directions of polarization axes of the first polarizer 40 and the second polarizer 50 are perpendicular to each other and the sample S carried by the sample S carrying module 10 does not have birefringence property. When the sample S carried by the sample carrying module 10 has birefringence property, the light emitted from the light source 22 can pass through the second polarizer 50, the sample S, the lens module 30 and the first polarizer 40 in order, and finally reach the image capture module 61. Then, the operator can capture the image of the sample S by the image capture module 61. Besides, since the first polarizer 40 is fixed on the image capture module 61, the operator can rotate the base 21 to change the angle of the polarization axis of the second polarizer 50. This operation allows the light of different polarization angles to pass through the sample S for observing the structures of the sample S in different phases. For example, in the polarization mode, the micro structure of the starch crystals can be clearly observed without the dying process.

To be noted, the "detachably dispose" in the previous embodiment can be achieved by magnets. For example, at least one of the sample carrying module 10, the light source module 20 and the lens module 30 has a magnetic element. In one embodiment, the sample carrying module 10 includes a first magnetic element (not shown), and the light source module 20 has a second magnetic element (not shown) disposed in the base 21 and corresponding to the first magnetic element. Alternatively, the base 21 can be made of magnetic material. In addition, the lens module 30 may also include a third magnetic element (not shown) disposed in the lens base 32 and corresponding to the first magnetic element. Alternatively, the lens base 32 can be made of magnetic material. When the first magnetic element is a magnet, the second magnetic element and/or the third magnetic element can be magnet or magnetic metal. When the second magnetic element is a magnet, the first magnetic element can be a magnet or magnetic metal, and the third magnetic element can be a magnet. When the third magnetic element is a magnet, the first magnetic element can be a magnet or magnetic metal, and the second magnetic element can be a magnet.

As mentioned above, when the portable microscope apparatus 1 is cooperated with the portable electronic device 60, the lens module 30 is fixed on the portable electronic device 60, the sample carrying module 10 and the light source module 20 are assembled by the connection of the limiting member 114 and the restriction portion 212, and the lens module 30 and the sample carrying module 10 are detachably assembled by the magnets. In this case, the sample carrying module 10 and the light source module 20 are not relatively moved, and so are the lens module 30 and the portable electronic device 60. The sample carrying module 10 and the lens module 30 are relatively movable for moving the portable microscope apparatus 1 to place the sample S within the lens field of the portable electronic device 60.

Figure 2A:
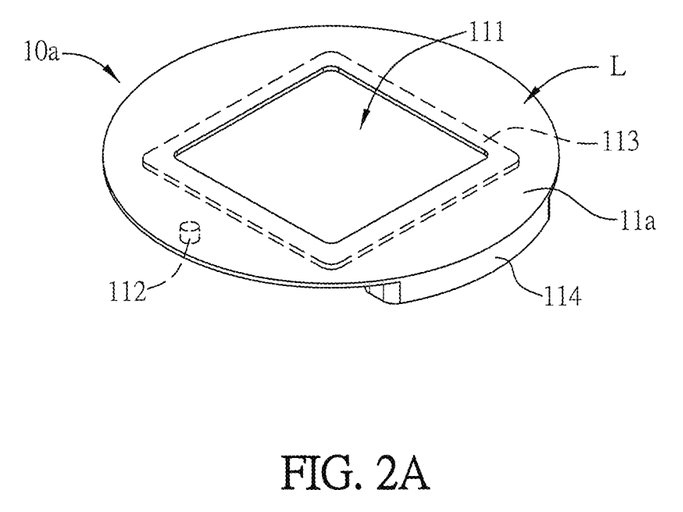
FIG. 2A is schematic diagram showing a sample carrying module according to an embodiment of the invention.
Figure 2B:
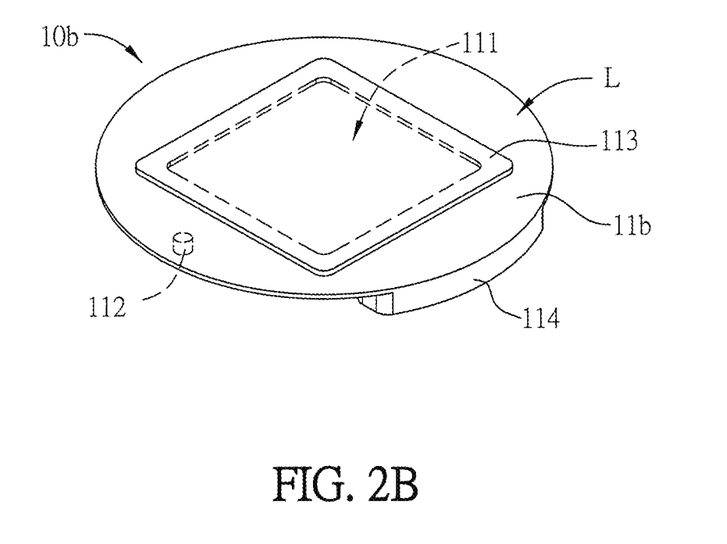
FIG. 2B is a schematic diagram showing a modification aspect of FIG. 2A.
Figure 2C:
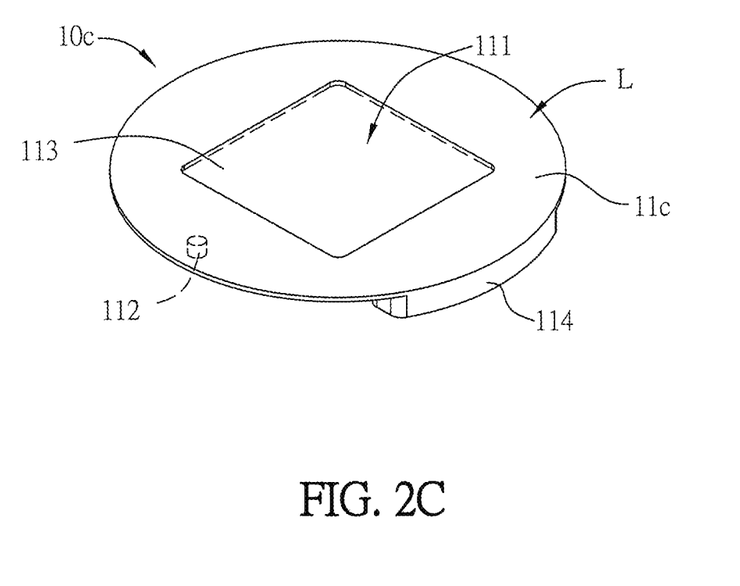
FIG. 2C is a schematic diagram showing another modification aspect of FIG. 2A.

FIG. 2A is schematic diagram showing a sample carrying module according to an embodiment of the invention, FIG. 2B is a schematic diagram showing a modification aspect of FIG. 2A, and FIG. 2C is a schematic diagram showing another modification aspect of FIG. 2A. Referring to FIGS. 2A to 2C, the sample carrying modules 10a, 10b and 10c are mostly similar to the sample carrying module 10. Different from the sample carrying module 10, each of the sample carrying modules 10a, 10b and 10c has a transparent element 113. To be noted, the adhesive element 12 is not shown in FIGS. 2A to 2C, and it will be described in the following examples. As shown in FIG. 2A, in the sample carrying modules 10a, the transparent element 113 is disposed at same side of the body 11 as the protrusion portion 112. As shown in FIG. 2B, in the sample carrying modules 10b, the transparent element 113 is disposed one side of the body 11 opposite to the protrusion portion 112. As shown in FIG. 2C, in the sample carrying modules 10c, the transparent element 113 is directly embedded within the light-transmission region 111. The transparent element 113 can be a glass plate, a plastic plate or a resin plate. To be noted, since the transparent element 113 is light permeable, it can introduce the environmental light if the environment is bright enough. In this case, the portable microscope apparatus 1 can still be operated without turning on the light source 22, and the image capture module 61 can observe the sample. Herein, the observed image may have the dark field effect.

Figure 3A:
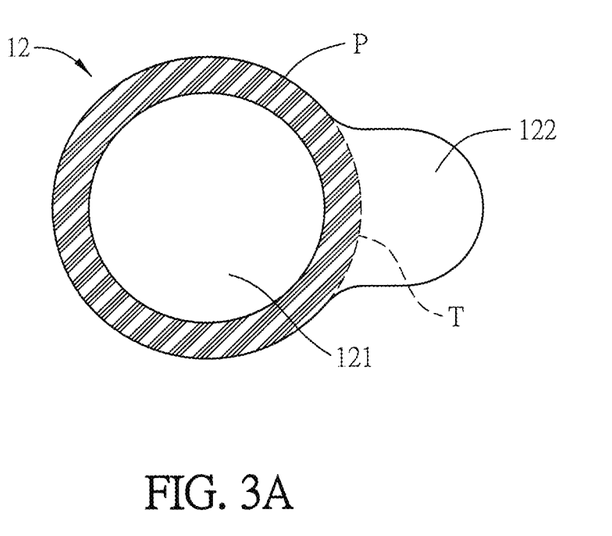
FIGS. 3A to 3E are top views of various aspects of the adhesive element of FIG. 1A.
Figure 3B:
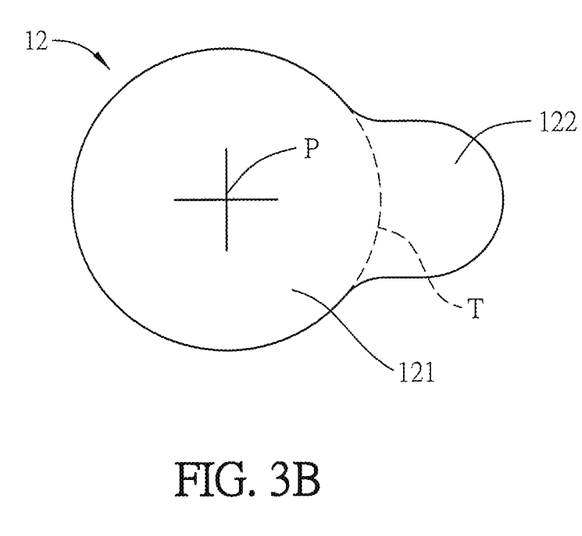
Figure 3C:
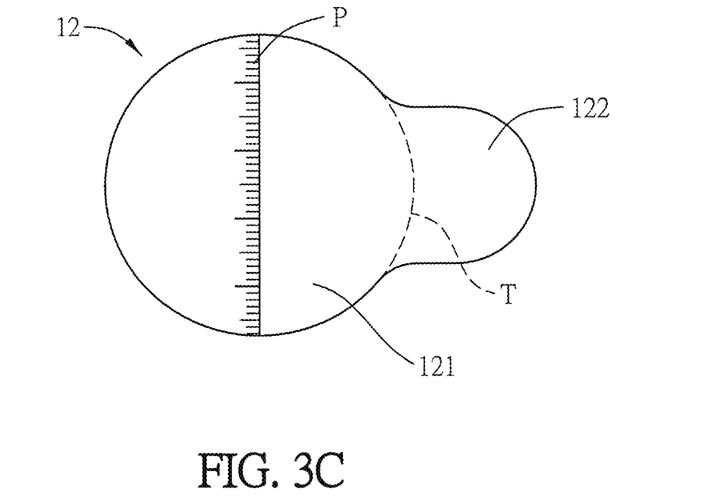

FIGS. 3A to 3E are top views of various aspects of the adhesive element of FIG. 1A. Referring to FIGS. 3A to 3C, the adhesive element 12 can be a transparent element with a transmittance greater than 90%. The adhesive element 12 has an adhesive region 121 and a non-adhesive region 122. The adhesive region 121 is configured to stick the sample S, and then attached to the transparent element 113. The diameter of the adhesive region 121 is not greater than 2.5 cm. The operator can hold the non-adhesive region 122 for operation. In one embodiment, an easy tearing line T is configured between the adhesive region 121 and the non-adhesive region 122. When the operator wants to reserve the stuck sample S, the adhesive element 12 is attached to a reserve region (e.g. a sticking book or a glass slide), and the non-adhesive region 122 is teared away from the adhesive element 12. The adhesive region 121 of the adhesive element 12 (either the front side or the rear side is acceptable) has a pattern P for assisting observation. The pattern P can be a periodical geometric pattern or a complex figure formed by printing. When the user operates the portable microscope apparatus 1, the sample carrying module 10, 10a, 10b or 10c can be moved to adjust the sample S into the lens field of the image capture module 61. However, when the operator views through the portable microscope apparatus 1, it is still hard to distinguish the relative positions of the sample S and the lens field of the image capture module 61. In this case, the configuration of the pattern P can assist the operator to rapidly figure out the relative positions of the sample S and the lens field of the image capture module 61. In one embodiment, for example, the pattern P is configured at the edge of the adhesive region 121. As shown in FIG. 3A, when the user views the pattern P within the lens field of the image capture module 61, he/she can realize that the lens field of the image capture module 61 aligns to the edge of the adhesive region 121. Then, the operator can observe the sample S after properly moving the sample carrying module 10, 10a, 10b or 10c toward the opposite side. In another embodiment, the pattern P is a pointing pattern such as a circle, a star (*) or a cross (+). As shown in FIG. 3B, the pattern P is a cross pattern (+) located at the center of the adhesive region 121. When the user views the pattern P within the lens field of the image capture module 61, he/she can realize that the lens field of the image capture module 61 aligns to the center of the adhesive region 121. In addition, the operator may want to know the scale of the sample S when viewing through the portable microscope apparatus 1. Accordingly, in another embodiment as shown in FIG. 3C, the pattern P is a scale, so that the operator can directly measure the size of the sample S within the lens field of the image capture module 61.

Figure 3D:
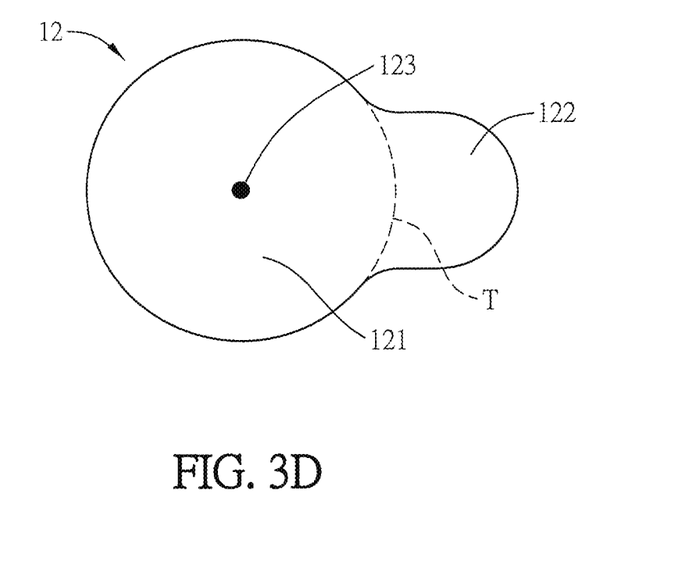

In addition, the adhesive element 12 can be configured with a light shielding region for forming a dark field. As shown in FIG. 3D, the adhesive region 121 has a transparent area 124 and a nontransparent area 123. In this aspect, the nontransparent area 123 is a printed black dot, which can be configured at the center of the adhesive region 121 or any position in the adhesive region 121 that can provide the desired dark field effect in the image. The nontransparent area 123 can also be constructed by a plurality of distributed printed black dots. Accordingly, it is possible to configure one or more printed black dots on the adhesive element 12, which is totally transparent, to form the light shielding region, so that the refracted or scattered light can be directed to the sample S so as to achieve the dark field effect and improve the resolution.

Figure 3E:
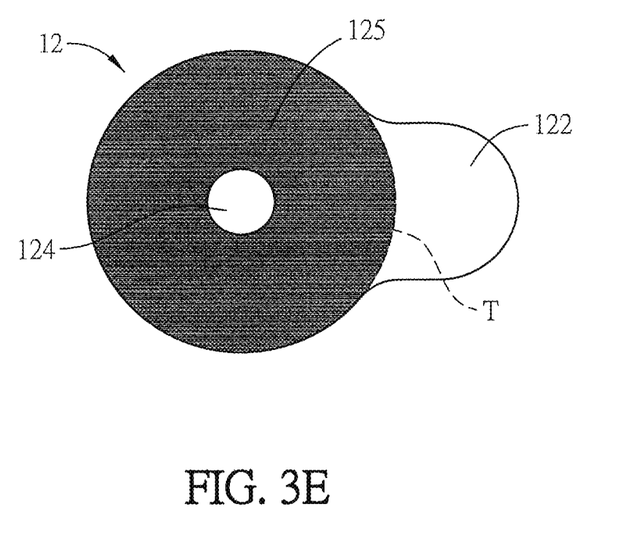

In another aspect, as shown in FIG. 3E, the adhesive region 121 includes a transparent area 126 and a nontransparent area 125. In this aspect, the nontransparent area 125 is a ring, which can be configured at the center of the adhesive region 121 or any position in the adhesive region 121 that can provide the desired dark field effect in the image. Accordingly, it is possible to configure a light shielding ring on the adhesive element 12, which is totally transparent, to form a dark field sticker. In addition, the aspects of FIGS. 3D and 3E can be combined. The aspect of dark field sticker can increase the contrast between the sample S and the background so as to obtain a better image.

Figure 4:
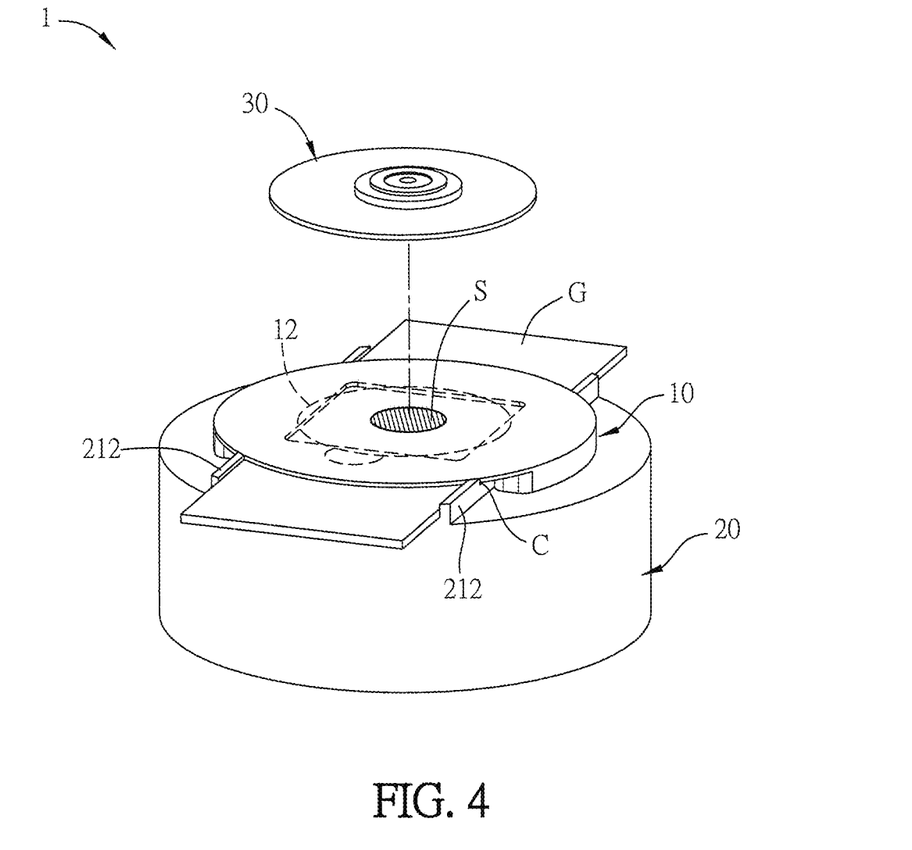
FIG. 4 is a schematic diagram showing a sample carrying module cooperated with a regular glass slide according to an embodiment of the invention.

In another embodiment, the sample carrying module 10 and the light source module 20 can be cooperated with a regular glass slide, so that the portable microscope apparatus 1 can be compatible with the conventional glass slide sample. FIG. 4 is a schematic diagram showing a sample carrying module cooperated with a regular glass slide according to an embodiment of the invention. Referring to FIG. 4, the regular glass slide G is engaged within the restriction portion 212, and the sample carrying module 10 is detachably disposed on the restriction portion 212 and engaged in the slot C. In this case, the sample carrying module 10 can slightly press the regular glass slide G to prevent the movement of the regular glass slide G in the restriction portion 212. In this embodiment, the adhesive element 12 can operate with the regular glass slide G In other words, the adhesive element 12 can be directly attached to the regular glass slide G for forming the observable slide specimen.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A sample carrying module cooperated with a light source module, comprising:
    a body having a light-transmission region; and
    an adhesive element configured to stick a sample and then detachably adhered to the body, wherein the adhesive element at least partially covers the light-transmission region,
    wherein the body has an outer surface and an inner surface, the outer surface faces a lens of a lens module, the inner surface faces away the lens, and the adhesive element adheres to the inner surface, the sample carrying module and the lens module are relatively movable,
    wherein the body includes a protrusion member toward the light source module to form a gap between the body and the light source module where the adhesive element is located.

2. The sample carrying module of claim 1, wherein the adhesive element is a transparent element.

3. The sample carrying module of claim 2, wherein the adhesive element is a sticker.

4. The sample carrying module of claim 1, wherein the adhesive element has a sample attaching surface configured with an adhesive region and a non-adhesive region.

5. The sample carrying module of claim 4, wherein the adhesive region has a pattern for assisting observation.

6. The sample carrying module of claim 4, wherein the adhesive region comprises a transparent area and a non-transparent area.

7. The sample carrying module of claim 1, further comprising:
    at least a first magnetic element disposed at one side of the body.

8. The sample carrying module of claim 1, wherein the body has a protrusion portion disposed at one side of the body.

9. A portable microscope apparatus cooperated with an image capture module, comprising:
    a sample carrying module comprising a body and an adhesive element, wherein the body has a light-transmission region, the adhesive element is configured to stick a sample and then detachably adhered to the body and at least partially covers the light-transmission region;
    a light source module detachably disposed at a side of the body, and comprising a base and a light source, wherein the base has an aperture, the sample carrying module is detachably disposed at a side of the aperture, and the light source is disposed in the base; and
    a lens module comprising at least one lens, wherein the lens module corresponds to the light source module, and is detachably and directly disposed at one side of the sample carrying module,
    wherein the body has an outer surface and an inner surface, the outer surface faces the lens, the inner surface faces away the lens, and the adhesive element adheres to the inner surface,
    wherein the adhesive element is between the body and the light source module, and the sample carrying module and the lens module are relatively movable for moving the portable microscope apparatus to place the sample within a lens field of the portable electronic device,
    wherein the body includes a protrusion member toward the light source module to form a op between the body and the light source module where the adhesive element is located.

10. The portable microscope apparatus of claim 9, wherein the adhesive element is a transparent element.

11. The portable microscope apparatus of claim 10, wherein the adhesive element is a sticker.

12. The portable microscope apparatus of claim 9, wherein the adhesive element has a sample attaching surface configured with an adhesive region and a non-adhesive region.

13. The portable microscope apparatus of claim 12, wherein the adhesive region has a pattern for assisting observation.

14. The portable microscope apparatus of claim 12, wherein the adhesive region comprises a transparent area and a nontransparent area.

15. The portable microscope apparatus of claim 9, wherein the sample carrying module further comprises at least a first magnetic element disposed at one side of the body and magnetically connected to the light source module or the lens module.

16. The portable microscope apparatus of claim 15, wherein the light source module further comprises a second magnetic element disposed in the base and magnetically connected to the sample carrying module or the lens module.

17. The portable microscope apparatus of claim 16, wherein the lens module further comprises a third magnetic element magnetically connected to the sample carrying module or the light source module.

18. The portable microscope apparatus of claim 9, further comprising:
   a first polarizer and a second polarizer disposed on optical paths at two sides of the sample carrying module, respectively.

19. The sample carrying module of claim 1, wherein a transparent element of the body is directly embedded within the light-transmission region, and a transparent area of an adhesive region of the adhesive element and the sample are adhered together to the inner surface of the transparent element of the body.

* * * * *